United States Patent
Arramon et al.

(10) Patent No.: US 7,935,122 B2
(45) Date of Patent: May 3, 2011

(54) CANNULA HAVING ASYMMETRICALLY-SHAPED THREADS

(75) Inventors: Yves P. Arramon, Sunnyvale, CA (US); George Delli-Santi, Scotts Valley, CA (US)

(73) Assignee: ArthroCare Corporation, Austin, TX (US)

( * ) Notice: Subject to any disclaimer, the term of this patent is extended or adjusted under 35 U.S.C. 154(b) by 1476 days.

(21) Appl. No.: 11/022,062

(22) Filed: Dec. 23, 2004

(65) Prior Publication Data

US 2006/0142779 A1    Jun. 29, 2006

(51) Int. Cl.
*A61B 17/58* (2006.01)
(52) U.S. Cl. .......................................... 606/92
(58) Field of Classification Search .............. 606/92, 606/300, 304, 309–318, 96; 623/17.11–17.16
See application file for complete search history.

(56) References Cited

U.S. PATENT DOCUMENTS

| | | | |
|---|---|---|---|
| 2,426,535 A | 8/1947 | Turkel | 128/2 |
| 2,919,692 A * | 1/1960 | Ackermann | 600/567 |
| 4,011,869 A | 3/1977 | Seiler, Jr. | 604/22 |
| 4,099,518 A | 7/1978 | Baylis et al. | 600/567 |
| 4,469,109 A | 9/1984 | Mehl | 600/566 |
| 4,576,534 A * | 3/1986 | Barth et al. | 411/412 |
| 4,670,008 A | 6/1987 | Von Albertini | 604/165 |
| 4,793,363 A | 12/1988 | Ausherman et al. | 600/567 |
| 4,838,282 A | 6/1989 | Strasser et al. | 600/567 |
| 4,921,479 A | 5/1990 | Grayzel | 604/53 |
| 4,969,888 A | 11/1990 | Scholten et al. | 606/94 |
| 4,986,814 A | 1/1991 | Burney et al. | 606/164.11 |
| 5,014,717 A | 5/1991 | Lohrmann | 600/567 |
| 5,041,120 A | 8/1991 | McColl et al. | 606/99 |
| 5,108,404 A | 4/1992 | Scholten et al. | 606/94 |
| 5,195,526 A | 3/1993 | Michelson | 600/431 |
| 5,341,816 A | 8/1994 | Allen | 600/567 |
| 5,364,372 A * | 11/1994 | Danks et al. | 604/264 |
| 5,372,583 A | 12/1994 | Roberts et al. | 604/506 |
| 5,456,267 A | 10/1995 | Stark | 128/898 |

(Continued)

FOREIGN PATENT DOCUMENTS

DE      4219563 A1    12/1993

(Continued)

OTHER PUBLICATIONS

Cotton et al., "Preoperative percutaneous injection of methyl methacrylate and N-butyl cyanoacrylate in vertebral hemangiomas" *Am J Neuroradiol*, 17:137-142, 1996.

(Continued)

*Primary Examiner* — Thomas C Barrett
*Assistant Examiner* — Michael J Araj
(74) *Attorney, Agent, or Firm* — Matthew Scheele; Brian Szymczak

(57) ABSTRACT

Methods and apparatus for performing a medical procedure which involves penetrating a bone structure are disclosed. According to one aspect of the present invention, a method for performing a surgical procedure includes introducing an assembly that includes a threaded cannula and a stylet into a bone structure. The threads have a shape that allows the cannula tip to be pushed into the bone body yet prevent the tip from being pulled out of the bone body. In one embodiment, the threads have a buttress shape. The method may also include applying a rotational motion, as for example a torque, to the threaded cannula to adjust the depth of insertion with respect to the implantation site when it is determined that the depth of insertion is to be adjusted.

11 Claims, 8 Drawing Sheets

U.S. PATENT DOCUMENTS

| | | | | |
|---|---|---|---|---|
| 5,458,579 | A | 10/1995 | Chodorow et al. | 604/165 |
| 5,476,102 | A | 12/1995 | Como et al. | 600/585 |
| 5,487,725 | A | 1/1996 | Peyman | 604/22 |
| 5,527,298 | A | 6/1996 | Vance et al. | 604/528 |
| 5,595,186 | A | 1/1997 | Rubinstein et al. | 600/567 |
| 5,660,186 | A | 8/1997 | Bachir | 600/562 |
| 5,735,867 | A | 4/1998 | Golser et al. | 606/185 |
| 5,788,702 | A | 8/1998 | Draenert | 606/92 |
| 5,827,305 | A | 10/1998 | Gordon | 606/159 |
| 5,857,995 | A | 1/1999 | Thomas et al. | 604/22 |
| 5,925,056 | A | 7/1999 | Thomas et al. | 606/180 |
| 5,997,485 | A | 12/1999 | Ahmadzadeh | 600/567 |
| 6,019,776 | A | 2/2000 | Preissman et al. | 606/185 |
| 6,033,411 | A | 3/2000 | Preissman | 606/99 |
| 6,080,115 | A | 6/2000 | Rubinstein | 600/567 |
| 6,086,543 | A | 7/2000 | Anderson et al. | 600/567 |
| 6,241,734 | B1 | 6/2001 | Scribner et al. | 606/93 |
| 6,248,110 | B1 | 6/2001 | Reiley et al. | 606/93 |
| 6,264,618 | B1* | 7/2001 | Landi et al. | 600/567 |
| 6,280,456 | B1 | 8/2001 | Scribner et al. | 606/192 |
| 6,348,055 | B1 | 2/2002 | Preissman | 606/94 |
| 6,361,504 | B1 | 3/2002 | Shin | 600/562 |
| 6,375,659 | B1* | 4/2002 | Erbe et al. | 606/94 |
| 6,416,484 | B1 | 7/2002 | Miller et al. | 600/564 |
| 6,468,279 | B1* | 10/2002 | Reo | 606/79 |
| 6,517,519 | B1 | 2/2003 | Rosen et al. | 604/164 |
| 6,575,919 | B1 | 6/2003 | Reiley et al. | 600/567 |
| 6,613,054 | B2 | 9/2003 | Scribner et al. | 606/93 |
| 6,679,886 | B2 | 1/2004 | Weikel et al. | 606/79 |
| 7,048,743 | B2 | 5/2006 | Miller et al. | 606/94 |
| 7,081,122 | B1 | 7/2006 | Reiley et al. | 606/185 |
| 7,160,305 | B2 | 1/2007 | Schmieding | 606/80 |
| 7,572,263 | B2 | 8/2009 | Preissman | 604/224 |
| 2002/0188300 | A1 | 12/2002 | Arramon et al. | 606/93 |
| 2003/0236506 | A1 | 12/2003 | Schofield et al. | 604/272 |
| 2004/0082956 | A1* | 4/2004 | Baldwin et al. | 606/73 |
| 2004/0073139 | A1 | 8/2004 | Hirsch et al. | 600/564 |
| 2005/0021036 | A1* | 1/2005 | Whitmore et al. | 606/73 |
| 2005/0113843 | A1 | 5/2005 | Arramon | 600/432 |
| 2005/0276676 | A1* | 12/2005 | Mardinger et al. | 411/411 |
| 2006/0241627 | A1 | 10/2006 | Reo | 606/79 |
| 2007/0260255 | A1 | 11/2007 | Haddock et al. | 606/80 |

FOREIGN PATENT DOCUMENTS

| | | |
|---|---|---|
| DE | 4413520 A1 | 10/1995 |
| WO | 99/18865 | 4/1999 |
| WO | 99/18866 | 4/1999 |
| WO | 2006/071785 | 7/2006 |

OTHER PUBLICATIONS

Cybulski, "Methods of surgical stabilization for metastatic disease of the spine" *Neurosurgery*, 25:240-252, 1989.

Deramond et al., "Percutaneous vertebroplasty with methylmethacrylate: technique, method, results" *Radiology*, 117(supp.):352, 1990.

Galibert et al., "Note preliminaire sur le traitement des aniomes vertebraux par vertebroplastie acrylique percutanee" *Neurochirurgi*, 33:166-168. (Partial summary translation included), 1987.

Harrington, "Anterior decompression and stabilization of the spine as a treatment for vertebral collapse and spinal cord compression from metastatic malignancy" *Clinical Orthodpaedics and Related Research*, 233:177-197, 1988.

Kaemmerlen et al., "Vertebroplastie percutanee dans le traitement des metastases" *J. Radiol.*, 70(10):557-562. (Partial summary translation included), 1989.

Nicola et al., "Vertebral hemangioma: Retrograde embolization 0 Stabilization with methyl methacrylate" *Surg Neurol*, 27:481-486, 1987.

O'Donnell et al., "Recurrence of giant-cell tumors of the long bones after curettage and packing with cement" *J. of Bone and Joint Surg*, 76-A(12):1827-1833, 1994.

Persson et al., "Favourable results of acrylic cementation for giant-cell tumors" *Acta Orthop Scand*, 55:209-214, 1984.

Shapiro, "Cranioplasty, vertebral body replacement, and spinal fusion with tobramycin-impregnated methylmethacrylate" *Neurosurgery*, 28(6):789-791, 1991.

Stringham et al., "Percutaneous transpedicular biopsy of the spine" *Spine*, 19(17):1985-1991, 1994.

Sundaresan et al., "Treatment of neoplastic epidural cord compression by vertebral body resection and stabilization" *J. Neurosurg*, 63:676-684, 1985.

Wang, et al., "Safety of anterior cement fixation in the cervical spine: In vivo study of dog spine" *So. Medical J.* 77(2):178-179, 1984.

Weill et al., "Spinal metastases: Indications for and results of percutaneous injection of acrylic surgical cement" *Radiology*, 199(1):241-247, 1996.

Unknown author, "Trocar Entry Control", Research Disclosure, No. 38938, pp. 570-574, Sep. 1996.

KyphX® Express™ System, Kyphon Inc., 4 pgs, 2004.

KyphX® One-Step™ Osteo Introducer® System, Kyphon Inc., 2 pgs, 2004.

PCT Notification of the International Search Report for PCT/US98/21572, 6 pgs, Mailed Feb. 18, 1999.

PCT Notification of the Internatinal Search Report for PCT/US98/21662, 8 pgs, Mailed Feb. 18, 1999.

PCT Notification of the International Preliminary Examination Report for PCT/US98/21662, 8pgs, Mailed Nov. 30, 1999.

PCT Notification of the International Preliminary Examination Report for PCT/US98/21572, 15gs, Mailed Mar. 13, 2000.

PCT Notification of the International Search Report and Written Opinion for PCT/US05/46829, 6pgs, Mailed Oct. 18, 2006.

* cited by examiner

CANNULA HAVING ASYMMETRICALLY-SHAPED THREADS

BACKGROUND OF THE INVENTION

1. Field of Invention

The present invention relates generally to an apparatus for facilitating the formation of cavities in bone or tissue structures for therapeutic applications. More particularly, the present invention relates to cannulae which may be utilized to penetrate bone or other tissue for applications involving the injection of or the implantation of material into the bone or other tissue.

2. Description of the Related Art

In vertebroplasty, cancellous bone of the vertebrae is supplemented with bone "cement," e.g., polymethylmethacrylate (PMMA) or another filler material, in order to provide for anterior and posterior stabilization of the spine in various disease. As will be appreciated by those skilled in the art, a vertebra included in the spine includes an exterior formed from cortical bone, and an interior formed of cancellous or trabecular bone. Vertebroplasty often involves inserting a cannula into a target area of bone or tissue to achieve access to an implantation site for the bone cement.

Percutaneous vertebroplasty is desirable from the standpoint that it is minimally invasive as compared to a conventional alternative of surgically exposing a tissue site to be supplemented with bone cement. Several procedures are known for accessing a desired site in the cancellous bone of a vertebral body, or substantially any other cancellous bone, to deliver bone cement or any other suitable hard tissue implant material to stabilize, or build up, a site once expanded as taught by U.S. Pat. Nos. 6,280,456, 6,248,110, 5,108,404, and 4,969,888, which are each incorporated herein by reference.

To gain access to a hard tissue implantation site, as described in U.S. Pat. Nos. 6,019,776 and 6,933,411, which are each incorporated herein by reference, a straight needle or cannula in combination with a stylet may be employed. Once access is achieved and the stylet is removed from the cannula, bone cement may be delivered through the cannula for the purposes of filling the hard tissue implantation site. However, a shortcoming with the above mentioned straight cannula assembly is that once the cannula is driven into the bone body, there is no feature and/or structure to grip the bone wall and provide controlled advancement of the cannula.

Another cannula is shown in U.S. Pat. No. 6,679,886. Referring to FIG. 1, the prior art cannula includes threads at a distal portion. However, a shortcoming with the above mentioned threaded cannulae is that once the cannula is driven into the bone body, the threads are shaped such that the bone tends to be sheared as the cannula is inserted, destroying or stripping the bone wall. Consequently, controllably advancing the cannula is inhibited.

What is desirable is a cannula having a thread structure that facilitates convenient insertion, minimizes the damage to the bony wall, and maximizes the ability to be driven forward by the threads in a controlled manner.

SUMMARY OF THE INVENTION

The present invention relates to performing a medical procedure which involves penetrating a bone structure. According to one aspect of the present invention, a method for performing a surgical procedure includes introducing an assembly that includes a threaded cannula and a stylet into a bone structure wherein the threads have an asymmetric profile. The method also includes determining when a depth of insertion of the threaded cannula with respect to an implantation site of the bone structure is to be adjusted, and applying a rotational motion, as for example a torque, to the threaded cannula to adjust the depth of insertion with respect to the implantation site when it is determined that the depth of insertion of the threaded cannula with respect to the implantation site is to be adjusted.

In one embodiment, the method also includes withdrawing the threaded cannula from the bone structure, which may be a vertebral body, by causing the threaded cannula to rotate. In another embodiment, the method includes injecting bone cement into the implantation site, through an opening defined within the threaded cannula.

A cannula with asymmetric-shaped threads is capable of being pushed, driven or otherwise hammered into a bone structure or body, and precisely positioned through rotating the cannula. When sized appropriately, as for example such that a leading edge of an asymmetric thread has a slope relative to a first surface that has a magnitude which is significantly less steep than the magnitude of a slope of a trailing edge of the asymmetric thread relative to the same surface, the threads effectively enable the cannula to slide as well as rotate to move in a distal direction, while preventing the cannula from sliding to move in a proximal direction. The slopes associated with asymmetric threads at a distal end portion of a cannula may be selected to enable the cannula to be readily introduced and then driven into a bone structure without the application of a significant advancement force, to enable the cannula to be precisely positioned, and to effectively prevent the cannula from backing out of the bone.

In another aspect of the invention, the shape or profile of the threads enable the cannula assembly to be self tapping. The leading or forward thread surface is shallow and the trailing or backward thread surface is relatively steep. This profile tends to minimize the bone tissue's resistance to penetration, while maximizing the ability of the cannula to be driven forward by rotation.

According to another aspect of the present invention, a cannula for use in a medical procedure includes a distal end portion and at least one asymmetric thread that is disposed at the distal end portion. In one embodiment, the asymmetric thread includes a dual-start thread. In another embodiment, the asymmetric thread is a buttress thread.

According to another aspect of the present invention, a method for performing vertebroplasty includes introducing an assembly that includes a threaded cannula and a stylet into a vertebral body, and removing the stylet from within an opening defined within the threaded cannula once the assembly is introduced into the vertebral body. The method also includes coupling a bone cement delivery system to the threaded cannula, and injecting bone cement through the threaded cannula into the implantation site using the bone cement delivery system. It is then determined if a depth of insertion of the threaded cannula with respect to an implantation site of the vertebral body is to be adjusted. When it is determined that the depth of insertion is to be adjusted, a rotational motion is applied to the threaded cannula to adjust the depth of insertion with respect to the implantation site. Finally, the threaded cannula is withdrawn from the vertebral body by unthreading it from the bone when the procedure is completed.

These and other advantages of the present invention will become apparent upon reading the following detailed descriptions and studying the various figures of the drawings.

BRIEF DESCRIPTION OF THE DRAWINGS

The invention may best be understood by reference to the following description taken in conjunction with the accompanying drawings in which.

DETAILED DESCRIPTION OF THE EMBODIMENTS

Figure 1:
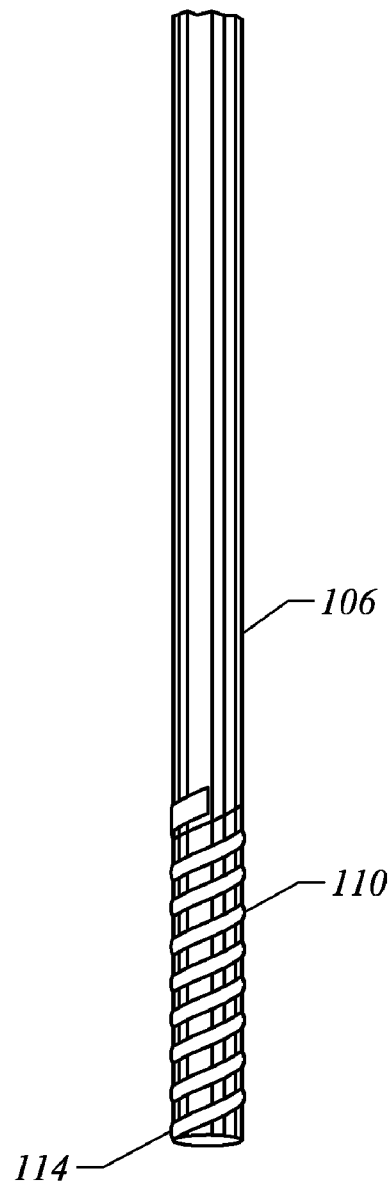
FIG. 1 is a diagrammatic representation of a portion of a shaft of a cannula with threads at a distal portion.

In further describing the subject invention, the subject devices and systems will be described first followed by a description of the subject methods and a summary of the kits which include the subject devices for performing the subject methods.

Before the present invention is described in detail, it is to be understood that this invention is not limited to particular variations set forth herein as various changes or modifications may be made to the invention described and equivalents may be substituted without departing from the true spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The ability to precisely control the position of a cannula that is used for a surgical procedure such as vertebroplasty is desired to enhance the safety and success of the procedure.

Precise control of the translation of the cannula is particularly important for the safety of the procedure because there are some anatomic structures which must not be penetrated or otherwise compromised during such procedure. For example, blood vessels in the vicinity of the bone structure are to be strictly avoided.

Standard cannulae used for vertebroplasty procedures can be difficult to precisely position, as they generally do not include any physical features which would effectively allow for accurate positioning. Further, maintaining the position of a cannula once a desired position is found may be difficult, as the cannula may slip from the desired position.

By providing asymmetric threads on at least a distal portion of a cannula, the positioning of the cannula may be effectively controlled. Asymmetric threads such as buttress-type threads enable the distal portion of the cannula to be relatively easily driven through bone, while preventing the cannula from being pulled out of or backed out of the bone. The presence of asymmetric threads on at least the distal portion of a cannula also facilitates the positioning of the distal portion by effectively allowing a certain amount of rotational motion to translate into a certain amount of linear motion.

Figure 2A:
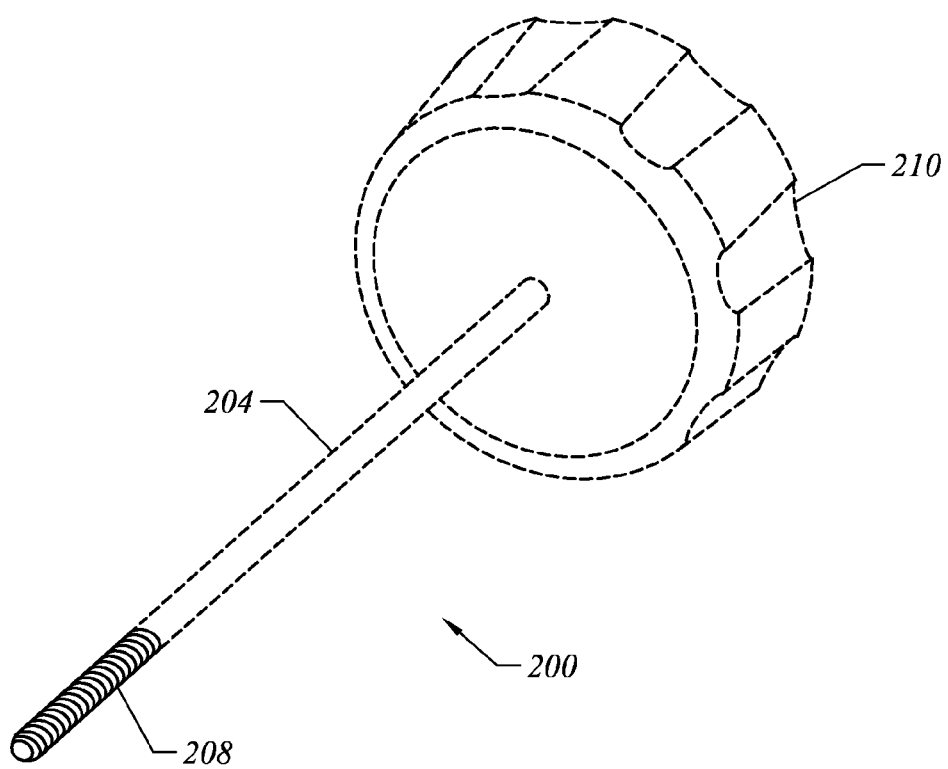
FIG. 2A is a diagrammatic representation of a portion of a cannula which includes an asymmetrically threaded distal portion in accordance with an embodiment of the present invention.

FIG. 2A is a diagrammatic representation of a portion of a cannula which includes an asymmetrically threaded distal portion in accordance with an embodiment of the present invention. A cannula portion 200 includes a shaft portion 204 and a threaded portion 208. Threaded portion 208 includes asymmetric threads, described below. In general, an opening or lumen defined within cannula portion 200 which enables a stylet (not shown) to be positioned therein to facilitate the penetration of threaded portion 208 into a bone structure such as a vertebral body. Additionally, a handle 210 may be connected at a proximal end of shaft.

The dimensions of threaded portion 208 may vary depending upon the requirements associated with the usage of cannula portion 200. In one embodiment, threaded portion 208 may include approximately twenty threads per inch, and may occupy approximately one inch of cannula portion 200, with a transition portion between threaded portion 208 and shaft portion 204 occupying approximately 0.25 inches. The outer diameter of threaded portion 208 and, hence, the outer diameter of shaft portion 204 may be up to about 0.2 inches or the outer diameter may have a gauge size in the range of, for example, between 13 and 8 gauge and preferably it is about an 11 gauge. It should be appreciated that the dimensions of threaded portion 208, and cannula portion 200 in general, may vary widely.

Figure 2B:
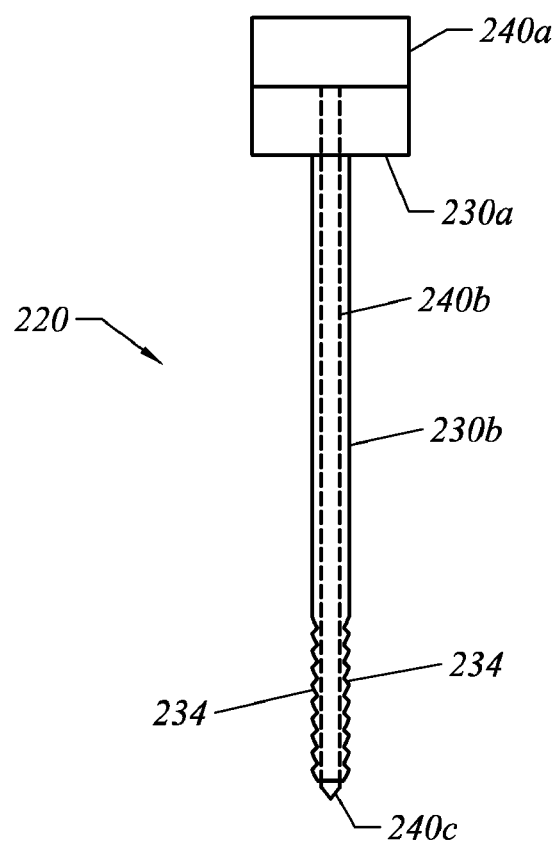
FIG. 2B is a diagrammatic representation of an assembly which includes an asymmetrically threaded cannula and a stylet in accordance with an embodiment of the present invention.
Figure 2C:
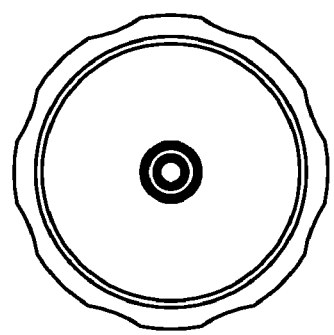
FIG. 2C is an end view of a cannula shown in FIG. 2A.

With reference to FIG. 2B, an assembly which is suitable for penetrating a bone structure will be described. FIG. 2B is a diagrammatic representation of an assembly which includes an asymmetrically threaded cannula and a stylet in accordance with an embodiment of the present invention. An assembly 220 includes a cannula which has a handle 230a that is coupled to a shaft or a body 230b. A distal portion of shaft 230b includes threads 234. Threads 234 will be discussed below with respect to FIGS. 3A-C.

A stylet which includes a handle 240a, a body 240b, and a tip 240c is arranged such that body 240b is positioned within an opening in shaft 230b. Body 240b is sized to enable the positioning of body 240b within shaft 230b, i.e., an outer diameter of body 240b is sized to be less than an inner diameter of shaft 230b. Tip 240c is arranged to protrude through the opening in shaft 230b when handle 240a is coupled to handle 230b.

Figure 3A:
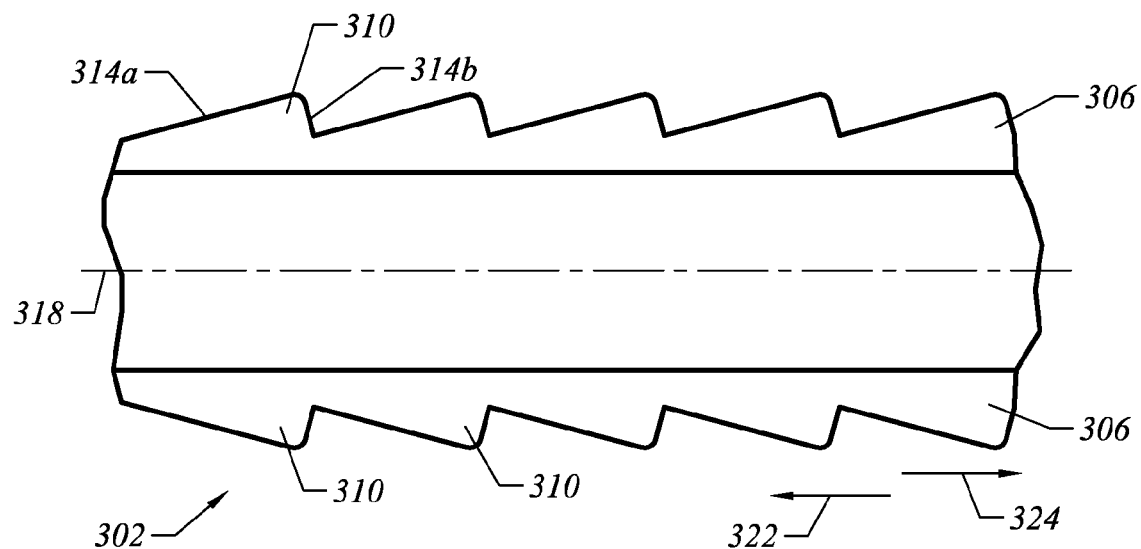
FIG. 3A is a diagrammatic cross-sectional side-view representation of an asymmetrically threaded portion of a cannula in accordance with an embodiment of the present invention.

The asymmetric threads located at a distal portion of a cannula may have various shapes and profiles such as, e.g., a buttress, fish-hook, or anchor-type shape. Referring next to FIG. 3A, the shape of asymmetric threads at a distal portion of a cannula will be described in accordance with an embodiment of the present invention. FIG. 3A is a diagrammatic cross-sectional side-view representation of a threaded portion of a cannula. A portion 302 includes a wall 306 on which asymmetric threads 310 are formed. As shown, asymmetric threads 310 are such that a first, forward, or leading edge 314a of a thread 310 has a slope of a different magnitude than a second, backward, or trailing edge 314b of thread 310 relative to a horizontal axis 318 of portion 302. Since each individual thread 310 is such that there is no axis about which the individual thread 310 is symmetric, the profile of each thread 310 is asymmetric. First edge 314a and second edge 314b are further arranged to have substantially different lengths, in one embodiment.

Threads 310 are shaped and sized to enable portion 302 to be readily pushed, hammered, or tapped into a bone structure without undue resistance and substantially without rotational motion in a distal direction indicated by arrow 320, while preventing portion 302 from being easily pulled out of the bone structure without rotational motion or without a significant force in a proximal direction indicated by arrow 324. That is, the shape and the size of threads 310 are typically selected based on a desired tradeoff between ease of insertion in a distal direction and resistance to withdrawal in a proximal direction. Threads 310 also enable controlled positioning of portion 302 through rotational motion. In general, the shape and the size of threads 310 may be chosen based on factors such as the cohesiveness of the material from which threads 310 are formed, and the coefficient of friction associated with the material. The shape and the size of threads 310 are also typically chosen based upon the type of bone material through which threads 310 are intended to penetrate.

Figure 3B:
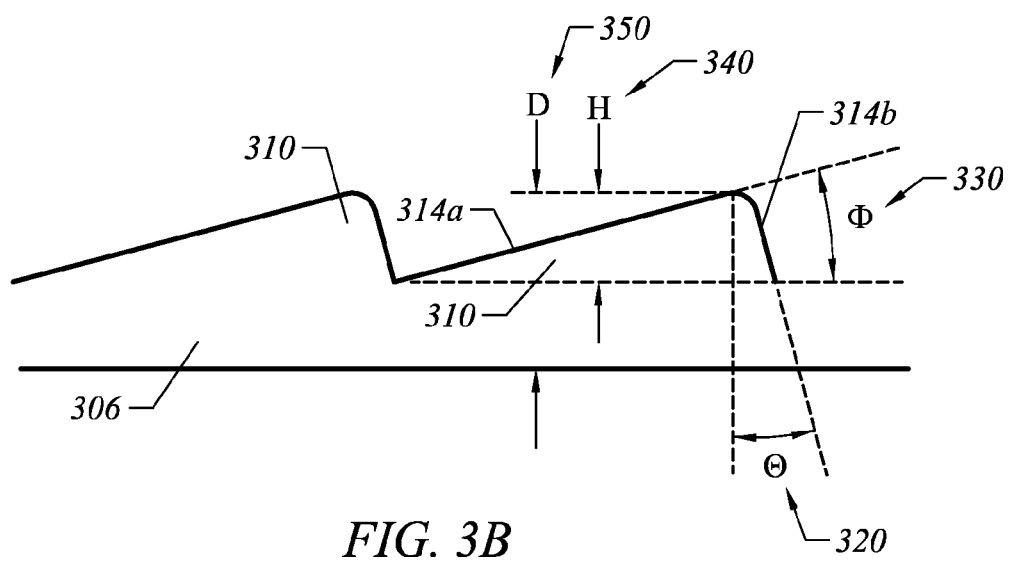
FIG. 3B is a geometric representation of asymmetric threads, i.e., threads 310 of FIG. 3A, in accordance with an embodiment of the present invention.

FIG. 3B is a geometric representation of asymmetric threads, i.e., threads 310 of FIG. 3A, in accordance with an embodiment of the present invention. A slope Φ 330 of first edge 314a of thread 310 is generally less than approximately sixty degrees. Preferably, slope Φ 330 is in the range of between approximately five degrees to approximately ten degrees. In one embodiment, slope Φ 330 is approximately seven degrees.

A slope Θ 320 associated with second edge 314b of thread 310 is typically in the range of between approximately five degrees to approximately ten degrees, as for example approximately seven degrees. However, it should be appreciated that slope Θ 320 may have substantially any angle that is less than approximately sixty degrees. It should be appreciated that as shown in FIG. 3b, slope Φ 330 and slope Θ 320 are measured relative to different reference points, i.e., slope Φ 330 is measured with respect to a horizontal axis and slope Θ 320 is measured with respect to a vertical axis. Hence, although slope Φ 330 and slope Θ 320, as defined by their respective reference points, may have similar ranges, threads 310 are asymmetric. That is, even when both slope Φ 330 and slope Θ 320 are both approximately seven degrees, for example, threads 310 are still asymmetric because slope Φ 330 is measured relative to a horizontal axis and slope Θ 320 is measured relative to a vertical axis.

Like slope Φ 330 and slope Θ 320, a height H 340 of a thread 310 relative to a base of thread 310 and a height D 350 of a thread 310 relative to an inner diameter of wall 306 may also be widely varied. Although height H 340 may have a value of approximately 0.006 inches in one preferred embodiment, height H 340 may generally have substantially any height, as for example a height in the range of between approximately 0.003 inches and 0.01 inches. Height D 350 may be in the range of, for example, approximately 10% to 14% of the diameter of the cannula. In a preferred embodiment, when height H 340 has a value of approximately 0.006 inches, height D 350 may have a value of approximately 0.016 inches. H may be 40% to 60% of dimension D. Additionally, Φ 330 may be in the range of, for example, 2 to 50 degrees and slope Θ 320 may be in the range of, for example, −20 to 20 degrees.

Another consideration of selecting the shape of the threads is to facilitate insertion of the cannula without damaging passageway integrity. Consequently, the low angle threads may bite and grip the bone wall. In contrast, threads that have a symmetric profile tend to strip the passageway wall when hammered into the bone. Threads cannot grip or be controlled in a stripped passageway.

A cannula which includes threads with an asymmetric profile may also include symmetric-profile threads. The thread profile may vary along the cannula. In the embodiment shown in FIG. 4, the thread profile varies progressively from asymmetric to symmetric. The pitch is constant in this embodiment.

Figure 4:
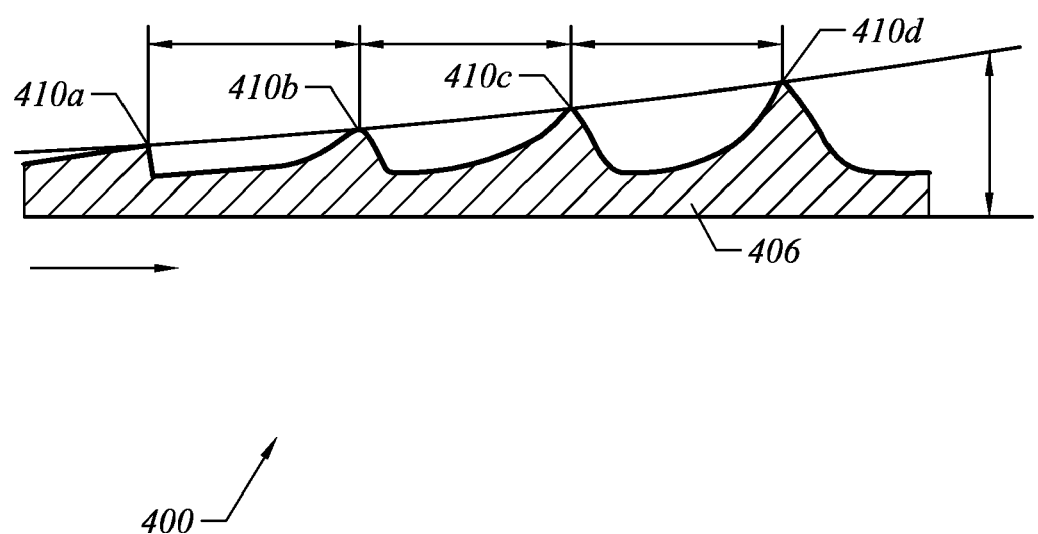
FIG. 4 is diagrammatic cross-sectional side-view representation of a distal portion of a cannula which includes both asymmetric threads and symmetric threads in accordance with an embodiment of the present invention.

Relatively precise positioning control using asymmetric threads may be achieved when substantially only the threads at the most distal end of the distal end portion of the cannula are asymmetric, while the threads that are at the more proximal end of the distal end portion are symmetric. The number of asymmetric threads may be chosen to be enough to enable the distal end portion to be driven into a bone structure and gain purchase. FIG. 4 is a partial diagrammatic cross-sectional side-view representation of a distal portion of a cannula which includes both asymmetric threads and symmetric threads in accordance with an embodiment of the present invention. A portion 400 of a cannula includes a wall 406 on which threads 410a, 410b, 410c, 410d are formed. Threads 410a, which are closer to a distal tip of the cannula, have an asymmetric profile, whereas threads 410d have a symmetric profile. While threads 410d are shown as having substantially triangular profiles, it should be appreciated that threads 410d may have any suitable symmetric profile, e.g., a substantially trapezoidal profile. Also, the threads may vary progressively, or immediately from 410*a* to 410*d*.

Figure 5:
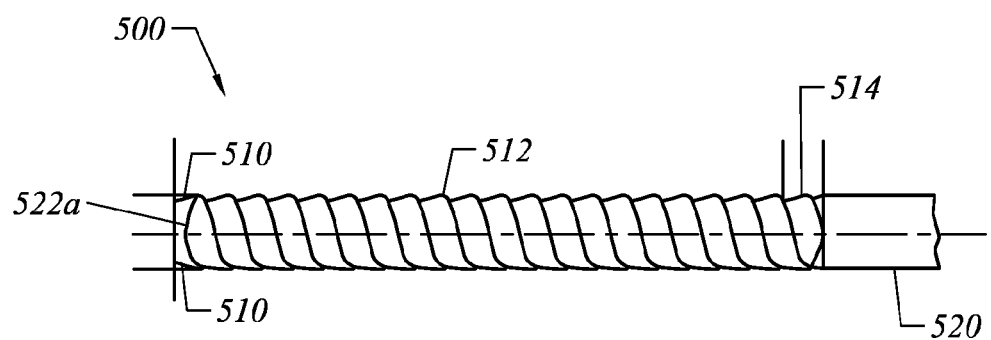
FIG. 5 is a diagrammatic representation of a distal tip of an asymmetrically threaded cannula which includes a dual-start thread in accordance with an embodiment of the present invention.

FIG. 5 is a diagrammatic representation of a distal tip of an asymmetrically threaded cannula which includes a dual-start thread in accordance with an embodiment of the present invention. Distal tip 500 includes a dual-start area 510 of threads 512, as well as a thread transition area 514 between threads 512 and an shaft portion 520 of the overall cannula which includes distal tip 500. When distal tip 500 is introduced into a bone structure, dual-start area 510 contacts the bone structure and facilitates the introduction of the remainder of distal tip 500 into the bone structure. Dual start tip allows threads to gain purchase at one or two vertices (522 *a,b*).

Figure 6:
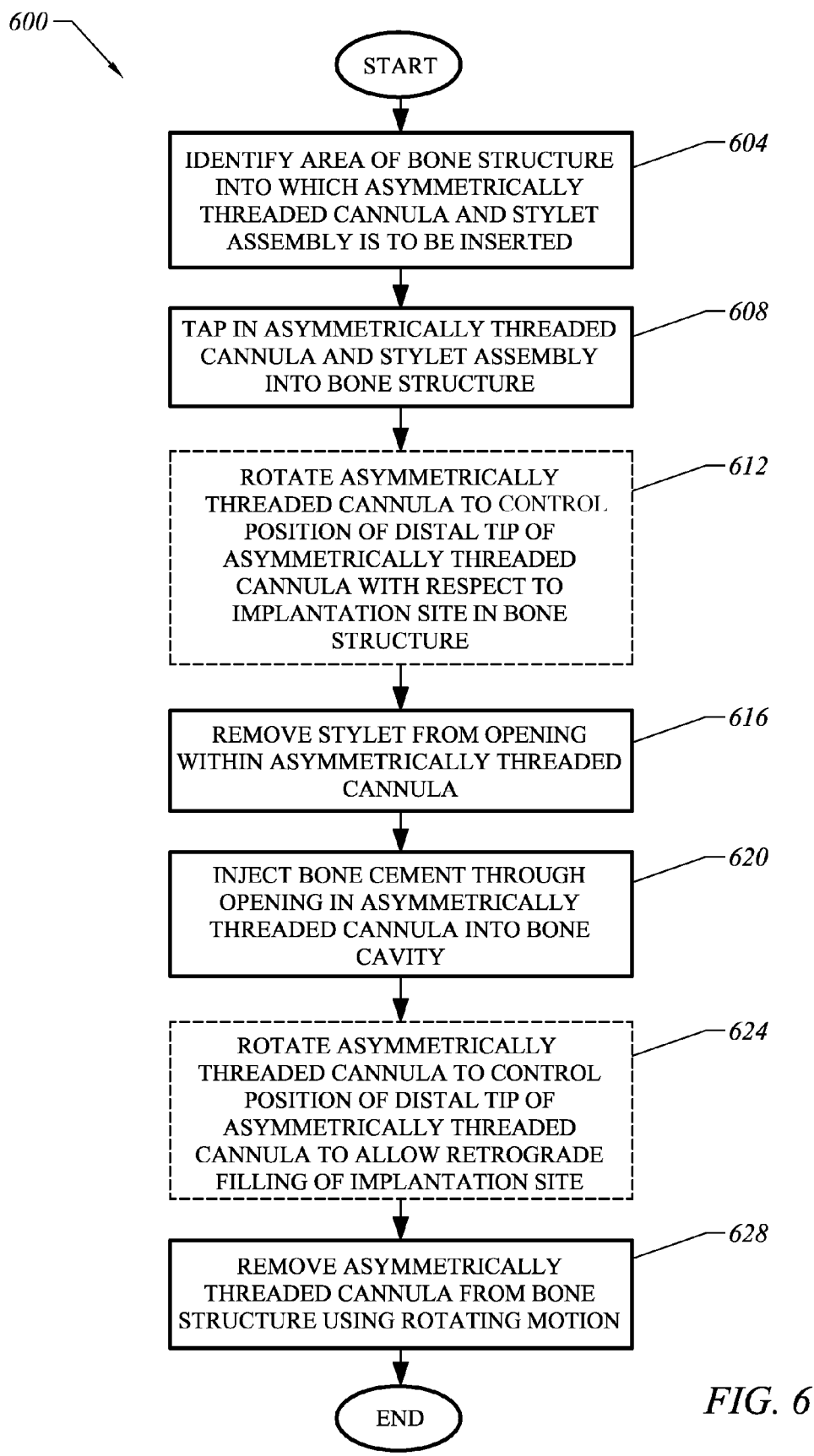
FIG. 6 is a process flow diagram which illustrates the steps associated with one method of performing a vertebroplasty procedure using an asymmetrically threaded cannula in accordance with an embodiment of the present invention.

With reference to FIG. 6, one method of performing a vertebroplasty procedure using a cannula with an asymmetrically threaded distal portion will be described in accordance with an embodiment of the present invention. It should be appreciated that various steps which are typically included in a vertebroplasty procedure are not described for ease of discussion. Such steps may include, but are not limited to, the anesthetization of skin in the vicinity of the bone structure which is to be penetrated, the preparation of bone cement, the verification of the proper positioning of the tip of the cannula, and the determination of when sufficient bone cement has been injected into an implantation site.

A process 600 of performing a vertebroplasty procedure begins at step 604 in which an area of a bone structure, e.g., an area of a vertebral body, into which an asymmetrically threaded cannula and stylet assembly is to be inserted is identified. A surgeon or a user may identify an external landmark which is to be penetrated in order to access the target area of a bone structure within the patient. Such identification process may be visually assisted by fluoroscopy or other imaging techniques known in the surgical arts. Once the area of the bone structure is identified, the asymmetrically threaded cannula and stylet assembly is tapped into the bone structure in step 608. The driving may be carried out using a mallet or other device which applies a force, as for example a non-rotational force, to the asymmetrically threaded cannula.

When necessary, in step 612, the asymmetrically threaded cannula may be advanced through rotation to control the position or depth of the distal tip of the asymmetrically threaded cannula with respect to an implantation site in the bone structure. It should be appreciated that although the asymmetrically threaded cannula may effectively be driven closer to the implantation site or backed further out from the implantation site substantially without utilizing the asymmetric threads, i.e., effectively without rotation, the ability to rotate the asymmetrically threaded cannula allows the amount by which the threaded cannula may be driven closer or backed further out from the implantation site to be controlled.

The pitch of the asymmetric threads is used to correlate the amount of rotation of the cannula to the amount by which the tip of the cannula may translate. Hence, by altering the pitch of the asymmetric threads, the amount by which the cannula moves distally or proximally for each 360 degree turn of the cannula may be varied. By way of example, in one embodiment, when there are approximately twenty threads per inch, one approximately 360 degree turn of the cannula in a clockwise direction may move the tip of the cannula forward or distally by approximately 2.5 millimeters [mm], while one approximately 360 degree turn of the cannula in a counter clockwise direction may back out the tip of the cannula or move the tip of the cannula proximally by approximately 2.5 mm.

From step 612, process flow moves to step 616 in which the stylet is removed from an opening defined within the shaft of the asymmetrically threaded cannula. Once the stylet is removed, bone cement, or a filler material, may be injected through the opening defined within the shaft of the asymmetrically threaded cannula into the implantation site in step 620. Typically, the injection of bone cement into the implantation site includes connecting flexible tubing to the cannula to enable the bone cement to be delivered.

During the course of injecting bone cement into the implantation site, in the event that the implantation site is a relatively large cavity, retrograde filling of the implantation site may be necessary. When retrograde filling is necessary, while bone cement is in the process of being injected into the implantation site, the asymmetrically threaded cannula is gradually backed out of, or moved proximally, with respect to the implantation site. Hence, when retrograde filling is used, the asymmetrically threaded cannula may be rotated in step 624 as needed to control the position of the distal tip of the asymmetrically threaded cannula to allow for retrograde filling. The ability to precisely control the position of the distal tip through the rotation of the asymmetrically threaded cannula reduces the likelihood that the bone cement will dry while the position of the distal tip is being adjusted.

In step 628, once the implantation site is sufficiently filled with bone cement, the asymmetrically threaded cannula is removed from the bone structure using a rotating motion. Upon removal of the asymmetrically threaded cannula, the process of performing a vertebroplasty procedure is completed.

Figure 7:
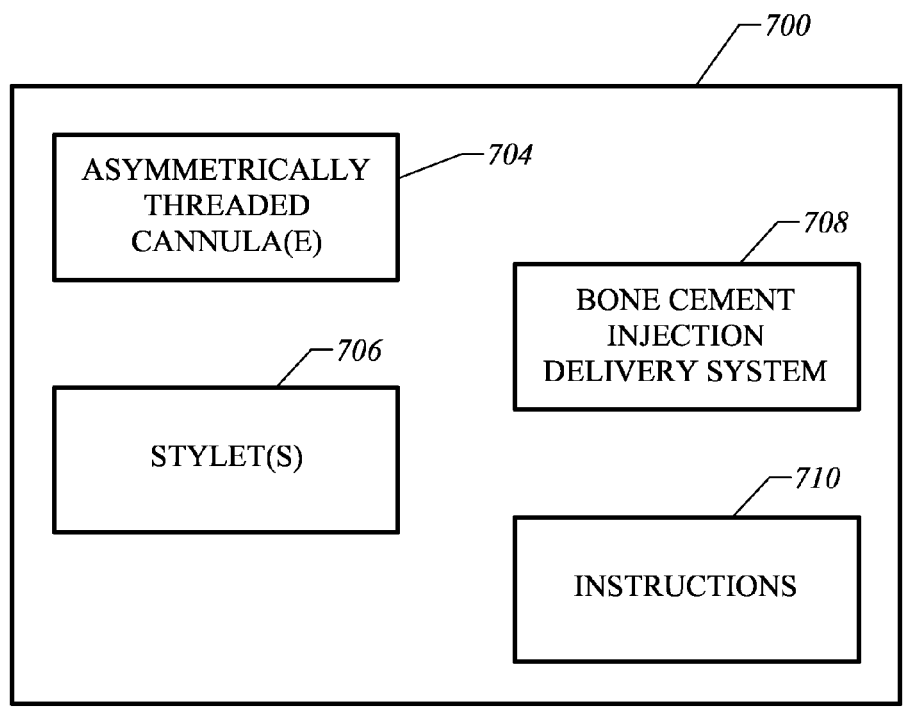
FIG. 7 is a block diagram representation of a kit in accordance with an embodiment of the present invention.

Also provided by the present invention are kits that include the devices as described above. FIG. 7 is a block diagram representation of a kit in accordance with an embodiment of the present invention. A kit 700 may include, but is not limited to including, at least one asymmetrically threaded cannula 704, a bone cement injection delivery system 708, and at least one stylet 706. It should be appreciated that a plurality of stylets 706 may be provided for use in a variety of applications. In addition, a subject kit such as kit 700 typically includes instructions 710 for using the subject systems, e.g., asymmetrically threaded cannula 704 and stylet 706, in methods according to the subject invention. Instructions 710 for practicing the subject methods are generally recorded on a suitable recording medium. For example, the instructions may be printed on a substrate, such as paper or plastic, etc. As such, instructions 710 may be present in the kits as a package insert or in the labeling of the container of the kit or components thereof, i.e., associated with the packaging or subpackaging. In other embodiments, instructions 710 are present as an electronic storage data file present on a suitable computer readable storage medium, e.g., CD-ROM, DVD, diskette, etc. In yet other embodiments, the actual instructions are not present in the kit, but means for obtaining the instructions from a remote source, e.g., via the Internet, are provided in lieu of instructions 710. An example of this embodiment is a kit that includes a web address where the instructions can be viewed and/or from which the instructions can be downloaded. As with the instructions, this means for obtaining the instructions is recorded on a suitable substrate.

Although only a few embodiments of the present invention have been described, it should be understood that the present invention may be embodied in many other specific forms without departing from the spirit or the scope of the present invention. By way of example, while a cannula with an asymmetrically threaded distal portion has been described as being suitable for use in vertebroplasty procedures involving vertebral bodies, such a cannula may be used with a variety of other medical, particularly surgical, procedures. In general, asymmetric threads may be implemented on substantially any cannula which is used to penetrate bone. Further, asymmetric threads may be applied to other surgical devices, e.g., a biopsy needle or a stylet, in which bone penetration or hard tissue penetration may be needed.

The pitch and the configuration of the asymmetric threads on a cannula may vary depending upon the type of bone the cannula is intended to penetrate. For example, the back edge of a thread may have a relatively steeper angle for the penetration of softer bone than for harder bone. Further, the front edge of a thread may also have a relatively steeper angle for softer bone than for harder bone. In addition, while an asymmetric thread has been described as being a buttress thread, an asymmetric thread may generally be substantially any type of thread which has an asymmetric profile and is suitable for facilitating the ability for the distal end portion of a cannula to slide distally through bone but not slide proximally through the bone. Threads with a generally barb-like profile, for instance, may be suitable for use.

In addition to the asymmetric threads of a cannula having a pitch and shapes that may vary, the size of an asymmetrically threaded cannula and the material from which such a cannula is formed may also vary. For instance, the cannula may be a 10.5 gauge cannula, or an 8 gauge cannula, and the cannula may be formed from any suitable biocompatible material. In one embodiment, the cannula may be formed from stainless steel.

While the asymmetric threads on a cannula have been described as being disposed on a distal end portion of the cannula, it should be appreciated that the asymmetric threads or threads in general are not limited to being disposed on the distal end portion of the cannula. In one embodiment, threads may extend past the distal end portion of the cannula, as for example substantially all the way to the proximal end of the cannula.

Additionally, threads may be provided on the stylet such that the stylet may bite into the bone or assist the cannula in biting into a bone structure. In a sense, asymmetric-shaped threads may adapt a standard cannula assembly into a self tapping cannula assembly. An example of a threaded stylet is shown in U.S. Pat. No. 6,383,190.

The formation of threads on a cannula may be achieved using any of a variety of different manufacturing processes. Manufacturing processes used to form the threads may include, but are not limited to, processes which utilize lathes, mills, and the like.

The steps associated with method of using a cannula with an asymmetrically threaded distal portion for a vertebroplasty procedure may vary widely. Steps may be added, removed, reordered, or altered without departing from the spirit or the scope of the present invention. By way of example, instead of rotating the cannula to advance the cannula with respect to an implementation site, the cannula may instead be driven distally with respect to the implementation site without benefit of rotation. Additionally, the cannula/stylet assembly may be used in a various surgical procedures such as, for example, biopsy procedures (as described in for example, U.S. patent application Ser. No. 10/269,926), bone cement injection procedures, and other types of surgical procedures where the advantages set forth herein.

Therefore, the present examples are to be considered as illustrative and not restrictive, and the invention is not to be limited to the details given herein, but may be modified within the scope of the appended claims.

What is claimed is:

1. A method for performing a surgical procedure comprising:
   introducing an assembly into a bone structure, the assembly including a threaded cannula wherein each thread comprises an asymmetric cross-section, and a stylet positioned at least partially within an opening defined within the threaded cannula, wherein the asymmetrical cross-section comprises a leading edge having a first slope and a trailing edge having a second slope and wherein the first slope is significantly less steep than the second slope;
   injecting bone cement through the threaded cannula into an implantation site;
   determining when a depth of insertion of the threaded cannula with respect to the implantation site of the bone structure is to be adjusted; and
   applying a rotational motion to the threaded cannula to bite and grip the bone structure and to adjust the depth of insertion with respect to the implantation site when it is determined that the depth of insertion of the threaded cannula with respect to the implantation site is to be adjusted;
   wherein said threaded cannula leading edge facilitates the cannula being pushed into the bone structure during the introduction step.

2. The method of claim 1 further including:
   withdrawing the threaded cannula from the bone structure, wherein withdrawing the threaded cannula from the bone structure includes rotating the threaded cannula.

3. The method of claim 1 further including:
   removing the stylet from within the opening defined within the threaded cannula.

4. The method of claim 1 further including:
   injecting the bone cement through the opening defined within the threaded cannula such that the implantation site is retrogradely filled.

5. The method of claim 1 wherein the surgical procedure is a vertebroplasty procedure, and the bone structure is a vertebral body.

6. The method of claim 1 wherein applying the rotational motion to the threaded cannula includes at least one of rotating the threaded cannula in a first direction to advance the threaded cannula distally and rotating the threaded cannula in a second direction to withdraw the threaded cannula proximally.

7. The method of claim 6 further including:
   driving the threaded cannula distally by applying a non-rotational force to the threaded cannula.

8. The method of claim 1 wherein introducing the assembly into the bone structure includes applying a force to the threaded cannula by driving the threaded cannula.

9. A method for performing vertebroplasty comprising:
   introducing an assembly into a vertebral body, the assembly including a cannula having threads with an asymmetric profile and a stylet positioned at least partially within an opening defined within the threaded cannula;
   removing the stylet from within the opening defined within the threaded cannula;
   coupling a bone cement delivery system to the threaded cannula;
   injecting bone cement through the threaded cannula into an implantation site using the bone cement delivery system;

determining when a depth of insertion of the threaded cannula with respect to the implantation site of the vertebral body is to be adjusted;

applying a rotational motion to the threaded cannula to adjust the depth of insertion with respect to the implantation site when it is determined that the depth of insertion of the threaded cannula with respect to the implantation site is to be adjusted; and withdrawing the threaded cannula from the vertebral body.

10. The method of claim 9 wherein the threaded cannula includes more than 10 asymmetric-shaped threads.

11. The method of claim 10 wherein the at least one asymmetric-shaped thread includes a first edge having a first slope relative to a first direction and a second edge having a second slope relative to a second direction that is approximately perpendicular to the first direction, the first slope having an angle of between approximately 3 degrees and approximately 50 degrees, the second slope having an angle of between approximately −10 degrees and approximately +10 degrees.

* * * * *